(12) United States Patent
Pike, Jr.

(10) Patent No.: US 10,987,163 B2
(45) Date of Patent: *Apr. 27, 2021

(54) TREATMENT OF ATRIAL FIBRILLATION USING HIGH-FREQUENCY PACING AND ABLATION OF RENAL NERVES

(71) Applicant: BIOSENSE WEBSTER (ISRAEL) LTD., Yokneam (IL)

(72) Inventor: Robert W. Pike, Jr., Coto de Caza, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/028,900

(22) Filed: Jul. 6, 2018

(65) Prior Publication Data

US 2018/0310991 A1 Nov. 1, 2018

Related U.S. Application Data

(63) Continuation of application No. 13/304,933, filed on Nov. 28, 2011, now Pat. No. 10,016,233.

(Continued)

(51) Int. Cl.
*A61B 18/14* (2006.01)
*A61B 18/02* (2006.01)
(Continued)

(52) U.S. Cl.
CPC .......... *A61B 18/1492* (2013.01); *A61B 18/02* (2013.01); *A61B 34/20* (2016.02);
(Continued)

(58) Field of Classification Search
CPC ................... A61B 2018/00577; A61B 18/1492
See application file for complete search history.

(56) References Cited

U.S. PATENT DOCUMENTS 5,329,988 A * 7/1994 Juger ............ F28D 1/0535
165/152
5,391,199 A 2/1995 Ben-Haim
(Continued)

FOREIGN PATENT DOCUMENTS

CN 1168625 A 12/1997
CN 1911157 A 2/2007
(Continued)

OTHER PUBLICATIONS

"Renal Denervation as a Therapeutic Approach for Hypertension, Novel Implications for an Old Concept" by M.P. Schlaich et al. Hypertension. Oct. 12, 2009. 54:1195-1201.*

(Continued)

*Primary Examiner* — Jason M Ip
(74) *Attorney, Agent, or Firm* — Etan S. Chatlynne; Roberts Calderon Safran & Cole P.C.

(57) ABSTRACT

An ablation catheter is equipped with an irrigated tip electrode that can stimulate tissue in, e.g., a renal artery to help identify the location of a renal nerve. High-frequency stimulation of the renal nerve causes a decrease in the blood pressure of the patient thereby indicating that a renal nerve is nearby. The ablation catheter is used to ablate the renal nerve using radiofrequency, ultrasound, microwave energy or cryogenic cooling. Irrigation from the irrigated tip electrode may be used to decrease damage to cells in the wall of the lumen of the renal artery other than the renal nerve, such as the endothelial cells. In order to treat atrial fibrillation an ablation catheter would be used to isolate one or more pulmonary veins.

17 Claims, 6 Drawing Sheets

Related U.S. Application Data

(60) Provisional application No. 61/420,047, filed on Dec. 6, 2010.

(51) Int. Cl.
*A61B 18/00* (2006.01)
*A61B 18/18* (2006.01)
*A61N 1/36* (2006.01)
*A61N 7/02* (2006.01)
*A61B 34/20* (2016.01)

(52) U.S. Cl.
CPC .............. *A61B 2018/00023* (2013.01); *A61B 2018/00404* (2013.01); *A61B 2018/00434* (2013.01); *A61B 2018/00511* (2013.01); *A61B 2018/1861* (2013.01); *A61B 2218/002* (2013.01); *A61N 1/36117* (2013.01); *A61N 7/022* (2013.01)

(56) References Cited

U.S. PATENT DOCUMENTS

| | | | |
|---|---|---|---|
| 5,545,161 A | 8/1996 | Imran | |
| 6,217,576 B1 | 4/2001 | Tu et al. | |
| 6,239,724 B1 | 5/2001 | Doron et al. | |
| 6,292,695 B1 | 9/2001 | Webster, Jr. et al. | |
| 6,332,089 B1 | 12/2001 | Acker et al. | |
| 6,484,118 B1 | 11/2002 | Govari | |
| 6,611,699 B2* | 8/2003 | Messing | A61B 18/1492 600/372 |
| 6,618,612 B1 | 9/2003 | Acker et al. | |
| 6,690,963 B2 | 2/2004 | Ben-Haim et al. | |
| 6,788,967 B2 | 9/2004 | Ben-Haim et al. | |
| 7,653,438 B2 | 1/2010 | Deem et al. | |
| 7,879,029 B2 | 2/2011 | Jimenez | |
| 8,583,220 B2 | 11/2013 | Schwartz | |
| 9,943,363 B2 | 4/2018 | Clark et al. | |
| 2002/0065455 A1 | 5/2002 | Ben-Haim et al. | |
| 2002/0165448 A1 | 11/2002 | Ben-Haim et al. | |
| 2003/0120150 A1 | 6/2003 | Govari | |
| 2004/0068178 A1 | 4/2004 | Govari | |
| 2005/0288730 A1 | 12/2005 | Deem et al. | |
| 2006/0041277 A1* | 2/2006 | Deem | A61N 1/0551 607/3 |
| 2007/0003826 A1 | 1/2007 | Hsu | |
| 2007/0029671 A1 | 2/2007 | Yamasaki | |
| 2007/0032826 A1 | 2/2007 | Schwartz | |
| 2007/0129761 A1 | 6/2007 | Demarais et al. | |
| 2007/0173899 A1 | 7/2007 | Levin et al. | |
| 2008/0045943 A1* | 2/2008 | Wittkampf | A61B 18/1492 606/41 |
| 2010/0222851 A1 | 9/2010 | Deem et al. | |
| 2010/0286684 A1 | 11/2010 | Hata et al. | |
| 2011/0270246 A1 | 11/2011 | Clark et al. | |

FOREIGN PATENT DOCUMENTS

| | | |
|---|---|---|
| CN | 101084038 A | 12/2007 |
| JP | 2007185505 A | 7/2007 |
| JP | 2008515544 A | 5/2008 |
| WO | 9605768 A1 | 2/1996 |
| WO | 9965561 A1 | 12/1999 |
| WO | 2011139589 A9 | 12/2011 |

OTHER PUBLICATIONS

Extended European Search Report for European Application No. 11191954, dated Mar. 7, 2012, 7 pages.
Japanese Notification of Reasons for Refusal issued in Japanese Application No. 2011-266111, dated Nov. 10, 2015, 4 pages.
Second Office Action for Chinese Application No. 201110419783.3, dated Aug. 11, 2015, 3 pages.

* cited by examiner

TREATMENT OF ATRIAL FIBRILLATION USING HIGH-FREQUENCY PACING AND ABLATION OF RENAL NERVES

CROSS-REFERENCE TO RELATED APPLICATIONS

The present application is a Continuation under 35 U.S.C. § 120 of U.S. patent application Ser. No. 13/304,933, filed Nov. 28, 2011, which claims priority under 35 U.S.C. § 119 to U.S. Provisional Patent Application No. 61/420,047, filed on Dec. 6, 2010. The entire contents of these applications are incorporated by reference herein in their entirety.

FIELD OF INVENTION

The present invention relates to a method of using ablation catheters for the treatment of cardiac arrhythmias, including atrial fibrillation, using a denervation of the renal nerve alone or in combination with ablation of cardiac tissue. In particular the method uses high-frequency pacing to identify the renal nerve for ablation and may include the use of ablation of cardiac tissue to achieve pulmonary vein isolation in the heart to treat drug-refractory cases of atrial fibrillation.

BACKGROUND OF INVENTION

Cardiac arrhythmias, and atrial fibrillation in particular, persist as common and dangerous medical ailments, especially in the aging population. In patients with normal sinus rhythm, the heart, which is comprised of atrial, ventricular, and excitatory conduction tissue, is electrically excited to beat in a synchronous, patterned fashion. In patients with cardiac arrhythmias, abnormal regions of cardiac tissue do not follow the synchronous beating cycle associated with normally conductive tissue as in patients with normal sinus rhythm. Instead, the abnormal regions of cardiac tissue aberrantly conduct to adjacent tissue, thereby disrupting the cardiac cycle into an asynchronous cardiac rhythm. Such abnormal conduction has been previously known to occur at various regions of the heart, such as, for example, in the region of the sino-atrial (SA) node, along the conduction pathways of the atrioventricular (AV) node and the Bundle of His, or in the cardiac muscle tissue forming the walls of the ventricular and atrial cardiac chambers.

Cardiac arrhythmias, including atrial arrhythmias, may be of a multiwavelet reentrant type, characterized by multiple asynchronous loops of electrical impulses that are scattered about the atrial chamber and are often self-propagating. Alternatively, or in addition to the multiwavelet reentrant type, cardiac arrhythmias may also have a focal origin, such as when an isolated region of tissue in an atrium fires autonomously in a rapid, repetitive fashion. Ventricular tachycardia (V-tach or VT) is a tachycardia, or fast heart rhythm that originates in one of the ventricles of the heart. This is a potentially life-threatening arrhythmia because it may lead to ventricular fibrillation and sudden death.

One type of arrhythmia, atrial fibrillation, occurs when the normal electrical impulses generated by the sinoatrial node are overwhelmed by disorganized electrical impulses that originate in the atria and pulmonary veins causing irregular impulses to be conducted to the ventricles. An irregular heartbeat results and may last from minutes to weeks, or even years. Atrial fibrillation (AF) is often a chronic condition that leads to a small increase in the risk of death often due to strokes. Risk increases with age. Approximately 8% of people over 80 having some amount of AF. Atrial fibrillation is often asymptomatic and is not in itself generally life-threatening, but it may result in palpitations, weakness, fainting, chest pain and congestive heart failure. Stroke risk increases during AF because blood may pool and form clots in the poorly contracting atria and the left atrial appendage. The first line of treatment for AF is medication that either slows the heart rate or reverts the heart rhythm back to normal. Additionally, persons with AF are often given anticoagulants to protect them from the risk of stroke. The use of such anticoagulants comes with its own risk of internal bleeding. In some patients, medication is not sufficient and their AF is deemed to be drug-refractory, i.e., untreatable with standard pharmacological interventions. Synchronized electrical cardioversion may also be used to convert AF to a normal heart rhythm. Alternatively, AF patients are treated by catheter ablation. Such ablation is not successful in all patients, however. Thus, there is a need to have an alternative treatment for such patients. Surgical ablation is one option but also has additional risks traditionally associated with surgery.

Diagnosis and treatment of cardiac arrhythmias include mapping the electrical properties of heart tissue, especially the endocardium and the heart volume, and selectively ablating cardiac tissue by application of energy. Such ablation can cease or modify the propagation of unwanted electrical signals from one portion of the heart to another. The ablation process destroys the unwanted electrical pathways by formation of non-conducting lesions. Various energy delivery modalities have been disclosed for forming lesions, and include use of microwave, laser and more commonly, radiofrequency energies to create conduction blocks along the cardiac tissue wall. In a two-step procedure—mapping followed by ablation—electrical activity at points within the heart is typically sensed and measured by advancing a catheter containing one or more electrical sensors (or electrodes) into the heart, and acquiring data at a multiplicity of points. These data are then utilized to select the endocardial target areas at which ablation is to be performed.

Electrode catheters have been in common use in medical practice for many years. They are used to stimulate and map electrical activity in the heart and to ablate sites of aberrant electrical activity. In use, the electrode catheter is inserted into a major vein or artery, e.g., femoral artery, and then guided into the chamber of the heart of concern. A typical ablation procedure involves the insertion of a catheter having a tip electrode at its distal end into a heart chamber. A reference electrode is provided, generally taped to the skin of the patient or by means of a second catheter that is positioned in or near the heart. RF (radio frequency) current is applied to the tip electrode of the ablating catheter, and current flows through the media that surrounds it, i.e., blood and tissue, toward the reference electrode. The distribution of current depends on the amount of electrode surface in contact with the tissue as compared to blood, which has a higher conductivity than the tissue. Heating of the tissue occurs due to its electrical resistance. The tissue is heated sufficiently to cause cellular destruction in the cardiac tissue resulting in formation of a lesion within the cardiac tissue which is electrically non-conductive. During this process, heating of the electrode also occurs as a result of conduction from the heated tissue to the electrode itself. If the electrode temperature becomes sufficiently high, possibly above 60 degrees C., a thin transparent coating of dehydrated blood protein can form on the surface of the electrode. If the temperature continues to rise, this dehydrated layer can become progressively thicker resulting in blood coagulation on the electrode surface. Because dehydrated biological material has a higher electrical resistance than endocardial tissue, impedance to the flow of electrical energy into the tissue also increases. If the impedance increases sufficiently, an impedance rise occurs and the catheter must be removed from the body and the tip electrode cleaned.

In U.S. Pat. No. 6,292,695 discloses a method of controlling cardiac fibrillation, tachycardia, or cardiac arrhythmia by the use of an electrophysiology catheter having a tip section that contains at least one stimulating electrode, the electrode being stably placed at a selected intravascular location. The electrode is connected to a stimulating means, and stimulation is applied across the wall of the vessel, transvascularly, to a sympathetic or parasympathetic nerve that innervates the heart at a strength sufficient to depolarize the nerve and effect the control of the heart.

The use of renal neurostimulation for the treatment of heart arrhythmias was disclosed in U.S. Patent Publication No. 2007/0129761 by Demarais et al. Demarais sets forth the use of neuromodulation to effectuate irreversible electroporation or electrofusion, ablation, necrosis and/or inducement of apoptosis, alteration of gene expression, action potential attenuation or blockade, changes in cytokine up-regulation and other conditions in target neural fibers. In some embodiments, such neuromodulation is achieved through application of neuromodulatory agents, thermal energy, or high intensity focused ultrasound.

In U.S. Patent Publication No. 2010/0222851 by Deem et al. the monitoring of renal neuromodulation was proposed stimulation to identify renal nerves to denervate or modulate. Stimulation of such nerves after prior to neural modulation would be expected to reduce blood flow while stimulation after neural modulation would not be expected to reduce blood flow to the same degree when utilizing similar situation parameters and locations prior to neural modulation.

SUMMARY OF THE INVENTION

The present invention is directed to a method for the treatment of patients, particularly, the treatment of cardiac arrhythmias such as atrial ablation using renal ablation alone or in combination with cardiac ablation.

The present method for the treatment of a patient comprises the steps of inserting an ablation catheter having an electrode mounted thereon into a renal artery of a patient wherein the renal artery has a wall defining a lumen, stimulating a portion of the wall of the lumen of the renal artery, monitoring the blood pressure of the patient, identifying a location on the renal wall of the tissue where the stimulation causes a decrease in the blood pressure of the patient thereby indicating the presence of a renal nerve near the location and ablating the renal nerve near the identified location.

Once the ablation has been done re-stimulating the identified location to determine whether the stimulation decreases the blood pressure of the patient and re-ablating the identified location to ablate the renal nerve if the there is a decrease may be necessary. The ablation catheter used may be one capable of ablating tissue using radiofrequency energy, ultrasound energy, microwave energy or cryogenic cooling. The ablation catheter may have an irrigated electrode to reduce damage to the wall of the renal artery other than the renal nerve cells, such as the endothelial layer. The irrigated electrode could have a plurality of holes through which a cooling fluid is capable of flowing or be cooled by a cooling fluid in a closed system. The cooling fluid may be saline and is preferably cooled substantially below the body temperature of the patient, more preferably, to approximately 20 degrees C.

The step of stimulating a portion of the wall of the lumen of the renal artery comprises using high-frequency pulses, preferably at a frequency greater than approximately 20 KHz to stimulate the renal nerve thereby causing a blood pressure response in the patient. The ablation catheter may be moved to a second location along the wall of the renal artery and the steps of stimulating, monitoring, identifying and ablating may be repeated. This can be done until it is believed that all renal nerves have been denervated.

The method of claim 1 wherein the treatment is for a cardiac arrhythmia. For treatment of a cardiac arrhythmia the method preferably includes the steps of inserting an ablation catheter into the heart of a patient and ablating cardiac tissue using the ablation catheter in order to correct the cardiac arrhythmia. If the cardiac arrhythmia is atrial fibrillation then the step of ablating cardiac tissue results in the isolation of one or more pulmonary veins.

The ablation catheter used in the method may include a location sensor such as a magnetic location sensor capable of proving information with regard to the location of the tip of the ablation catheter.

BRIEF DESCRIPTION OF THE DRAWINGS

These and other features and advantages of the present invention will be better understood by reference to the following detailed description when considered in conjunction with the accompanying drawings wherein.

DETAILED DESCRIPTION OF THE INVENTION

Figure 1:
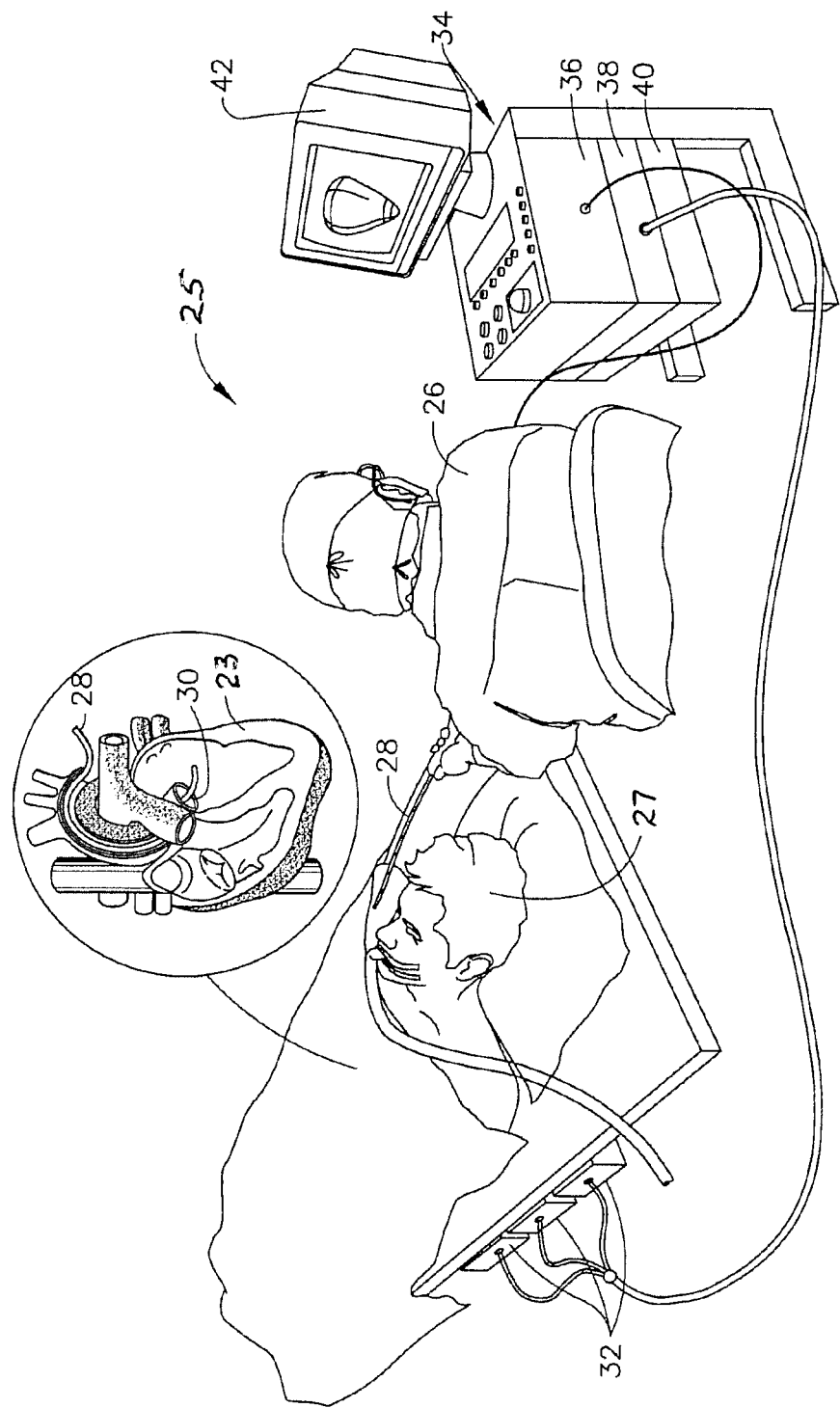
FIG. 1 is a schematic, pictorial illustration of a system for cardiac catheterization.

FIG. 1 is a schematic, pictorial illustration of a system 25 for renal and/or cardiac catheterization, in accordance with an embodiment of the present invention. System 25 may be based, for example, on the CARTO™ system, produced by Biosense Webster Inc. (Diamond Bar, Calif.). This system comprises an invasive probe in the form of a catheter 28 and a control console 34. In the embodiment described hereinbelow, it is assumed that catheter 28 is used in ablating endocardial tissue, as is known in the art. Alternatively, the catheter may be used mutatis mutandis, for other therapeutic and/or diagnostic purposes in the heart or in other body organs.

An operator 26, such as a cardiologist, inserts catheter 28 through the vascular system of a patient 27 so that a distal end 30 of the catheter enters a renal artery or a chamber of the patient's heart 23. The operator advances the catheter so that the distal tip of the catheter engages endocardial tissue at a desired location or locations. Catheter 28 is typically connected by a suitable connector at its proximal end to console 34. The console comprises a radio frequency (RF) generator 40, which supplies high-frequency electrical energy via the catheter for ablating tissue in the heart at the locations engaged by the distal tip, as described further hereinbelow. Alternatively, the catheter and system may be configured to perform ablation by other techniques that are known in the art, such as cryo-ablation, ultrasound ablation or ablation through the use of microwave energy.

Console 34 uses magnetic position sensing to determine position coordinates of distal end 30 inside heart 23. For this purpose, a driver circuit 38 in console 34 drives field generators 32 to generate magnetic fields within the body of patient 27. Typically, the field generators comprise coils, which are placed below the patient's torso at known positions external to the patient. These coils generate magnetic fields in a predefined working volume that contains heart 23. A magnetic field sensor within distal end 30 of catheter 28 (shown in FIG. 3) generates electrical signals in response to these magnetic fields. A signal processor 36 processes these signals in order to determine the position coordinates of the distal end, typically including both location and orientation coordinates. This method of position sensing is implemented in the above-mentioned CARTO system and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

Processor 36 typically comprises a general-purpose computer, with suitable front end and interface circuits for receiving signals from catheter 28 and controlling the other components of console 34. The processor may be programmed in software to carry out the functions that are described herein. The software may be downloaded to console 34 in electronic form, over a network, for example, or it may be provided on tangible media, such as optical, magnetic or electronic memory media. Alternatively, some or all of the functions of processor 36 may be carried out by dedicated or programmable digital hardware components. Based on the signals received from the catheter and other components of system 25, processor 36 drives a display 42 to give operator 26 visual feedback regarding the position of distal end 30 in the patient's body, as well as status information and guidance regarding the procedure that is in progress.

Alternatively or additionally, system 25 may comprise an automated mechanism for maneuvering and operating catheter 28 within the body of patient 27. Such mechanisms are typically capable of controlling both the longitudinal motion (advance/retract) of the catheter and transverse motion (deflection/steering) of the distal end of the catheter. Some mechanisms of this sort use DC magnetic fields for this purpose, for example. In such embodiments, processor 36 generates a control input for controlling the motion of the catheter based on the signals provided by the magnetic field sensor in the catheter. These signals are indicative of both the position of the distal end of the catheter and of force exerted on the distal end, as explained further hereinbelow.

Figure 2:
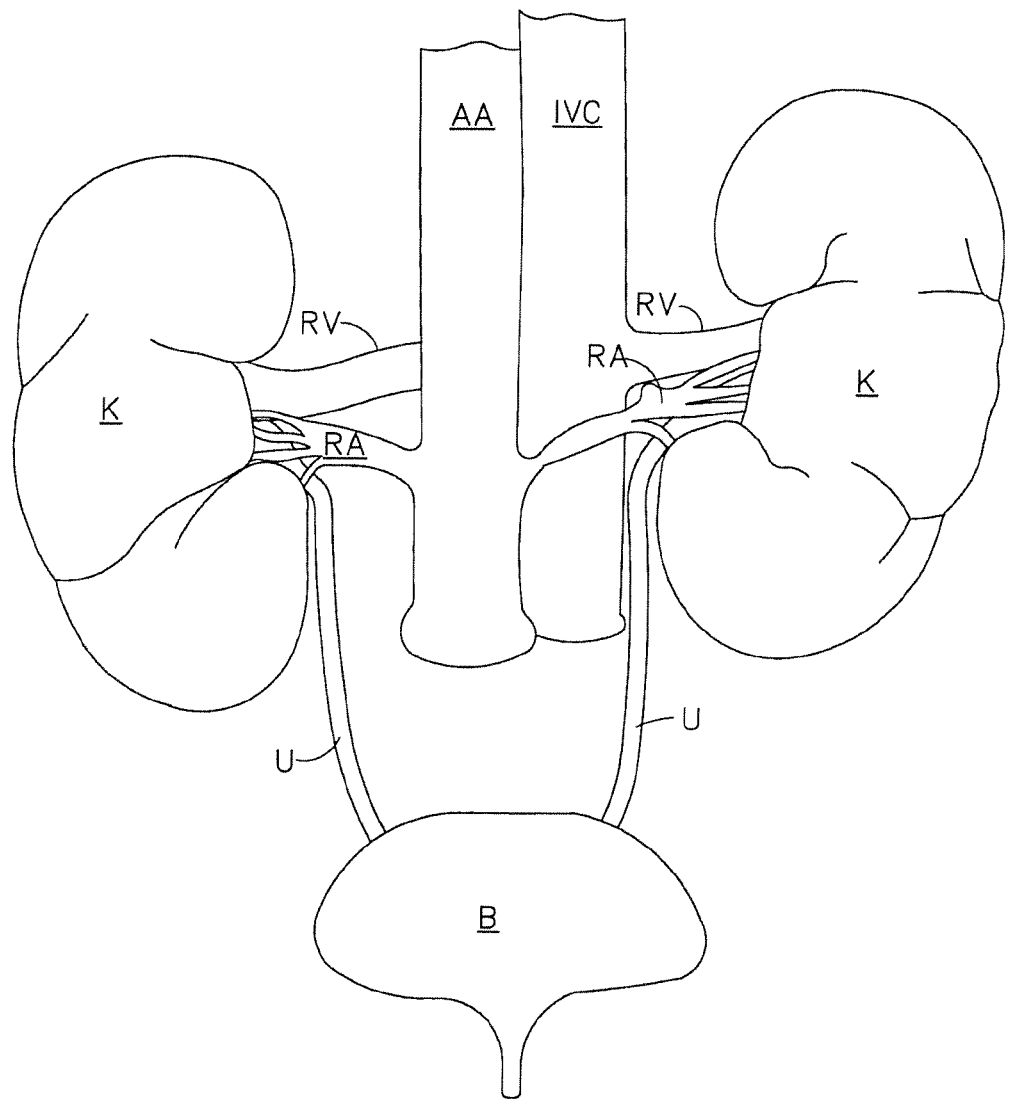
FIG. 2 is a schematic view illustrating the human renal anatomy.

FIG. 2 is a schematic illustration of human renal and urinary system which includes left and right kidneys K that are supplied with oxygenated blood by the renal arteries RA which are in turn supplied by the abdominal aorta AA. Despite their relatively small size, the kidneys receive approximately 20% of the total oxygenated blood output of the heart. Each renal artery branches into segmental arteries, dividing further into interlobar arteries which penetrate the renal capsule and extend through the renal columns between the renal pyramids. Urine is excreted by the kidneys K to the ureters U to the bladder B of the urinary system.

Figure 3:
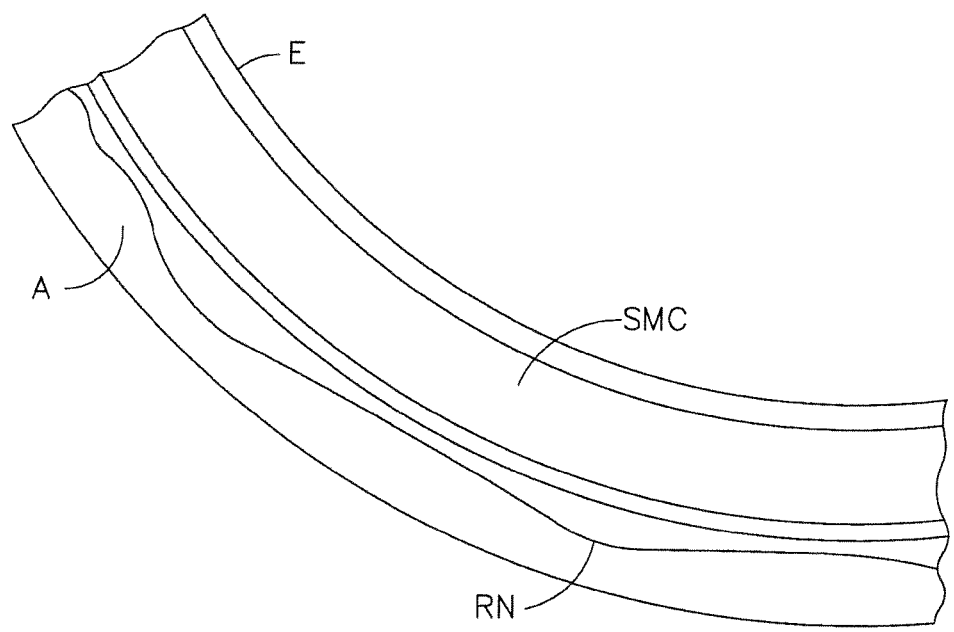
FIG. 3 is a schematic view of a cross section of a portion of the wall of a renal artery.

Once the oxygenated blood is used by the kidneys it flows from the kidneys back to the heart via the renal veins RV and the inferior vena cava IVC. The kidneys and the central nervous system communicate via the renal plexus, whose fibers course along the renal arteries to reach each kidney. Renal nerves extend longitudinally along the length of and around the renal arteries RA generally within the adventitia of the wall of the artery approximately 3 mm below the endothelial layer. FIG. 3 depicts the layers of the typical artery including the renal artery which include the endothelial layer E, the layer of smooth muscle cells SMC and the adventitia A. The renal nerve RN primarily resides within the adventitia.

Figure 4:
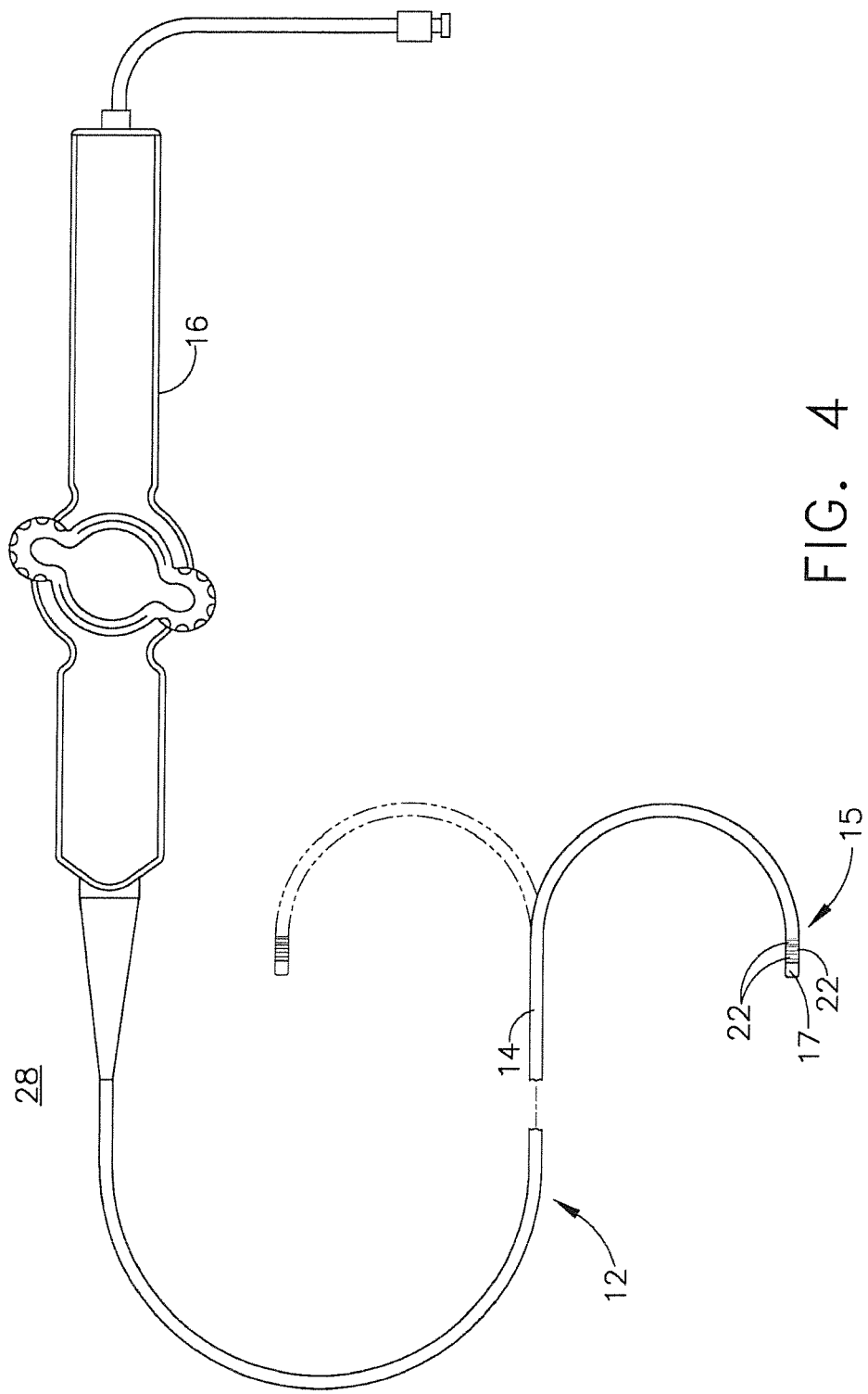
FIG. 4 is a side view of an embodiment of a catheter of the present invention.
Figure 5:
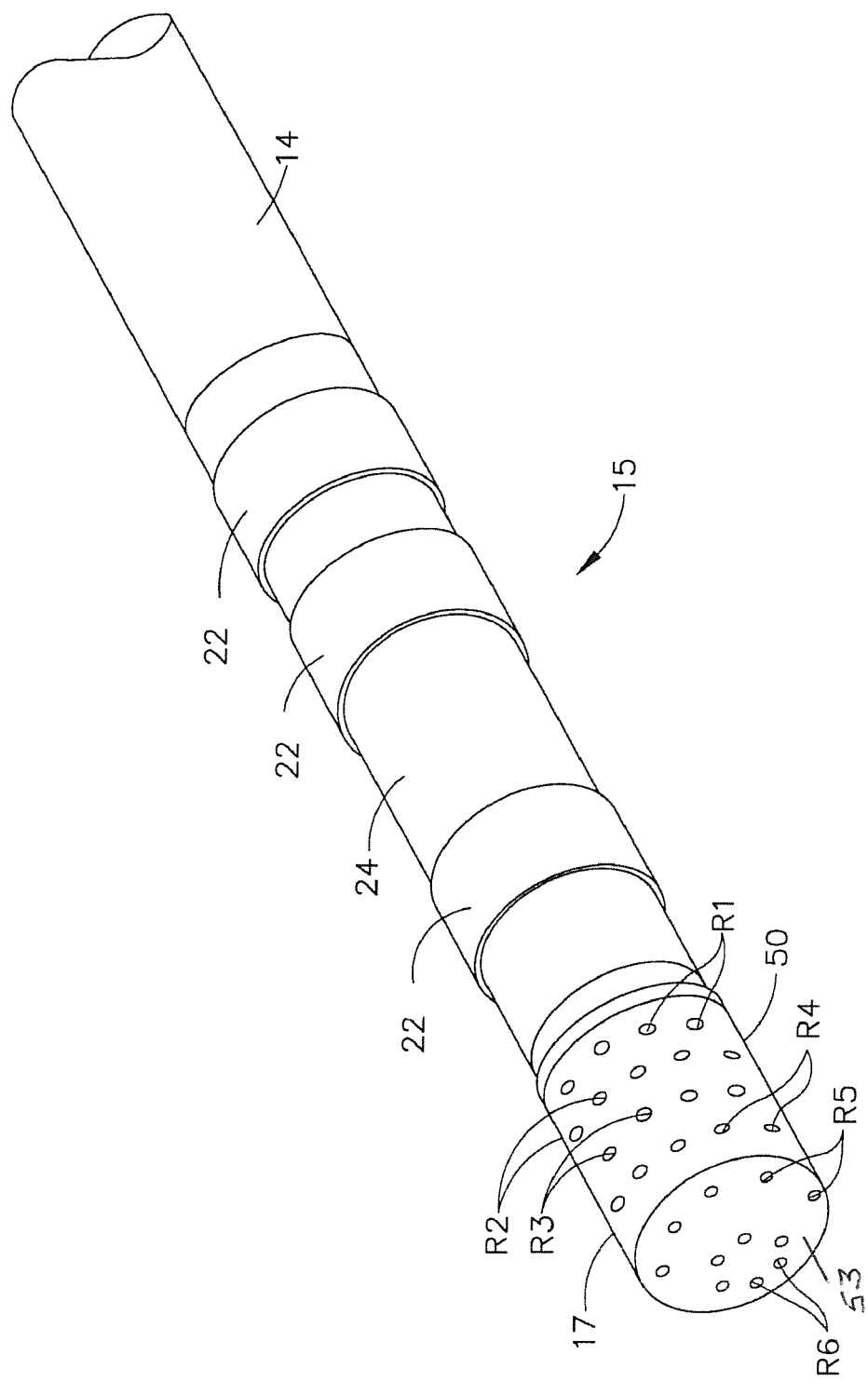
FIG. 5 is a perspective view of a distal section of the catheter of FIG. 4.

FIGS. 4 and 5 illustrate an embodiment of a catheter 28 with improved irrigation flow through a tip ablation electrode 17 for use in the present method. This catheter is more fully described in U.S. patent application Ser. No. 12/770,582 filed Apr. 29, 2010 which is hereby incorporated by reference. The tip electrode is configured to promote fluid flow into the tip electrode and dispersion of fluid therein in providing more uniform fluid coverage and flow at all locations on the exterior of the tip electrode. The catheter is therefore operable at lower flow rates with lower fluid load on the patient while providing improved cooling of the tip electrode than prior cooling electrodes. Moreover, a high fluid exit velocity at the tip electrode provides a "jetting" action that aids in creating a fluid boundary layer around the tip electrode which reduces the occurrence rate of char and/or thrombus during ablation. Fluid, e.g., saline or heparinized saline, can be transported to the ablation site from the tip electrode to cool tissue, reduce coagulation and/or facilitate the formation of deeper lesions. It is understood that other fluids can be delivered, as well, including any diagnostic and therapeutic fluids, such as neuroinhibitors and neuroexcitors.

The catheter 28 has an elongated catheter body 12 with proximal and distal ends, an intermediate deflectable section 14 at the distal end of the catheter body 12, and a distal section 15 with the irrigated mapping and ablation tip electrode 17. The catheter also includes a control handle 16 at the proximal end of the catheter body 12 for controlling deflection (single or bi-directional) of the intermediate section 14.

The catheter body 12 comprises an elongated tubular construction having a single, axial or central lumen (not shown). The catheter body 12 is flexible, i.e., bendable, but substantially non-compressible along its length. The catheter body 12 can be of any suitable construction and made of any suitable material. A presently preferred construction comprises an outer wall made of polyurethane or PEBAX. The outer wall comprises an imbedded braided mesh of stainless steel or the like to increase torsional stiffness of the catheter body 12 so that, when the control handle 16 is rotated, the intermediate section 14 of the catheter 28 will rotate in a corresponding manner.

The outer diameter of the catheter body 12 is not critical, but is preferably no more than about 8 french, more preferably 7 french. Likewise the thickness of the outer wall 20 is not critical, but is thin enough so that the central lumen can accommodate puller members, e.g., puller wires, lead wires, and any other desired wires, cables or tubings. If desired, the inner surface of the outer wall is lined with a stiffening tube to provide improved torsional stability Components that extend between the control handle 16 and the deflectable section 14 pass through the central lumen of the catheter body 12. These components include lead wires for the tip electrode 17 and ring electrodes 22 on the distal section 15, an irrigation tubing for delivering fluid to the distal section 15, a cable for a position location sensor carried in the distal section, puller wire(s) for deflecting the intermediate section 14, and a pair of thermocouple wires to sense temperature at the distal tip section 15.

At the distal end of the intermediate section 14 is the distal tip section 15 that includes the tip electrode 17 and a relatively short piece of connection tubing or covering 24 between the tip electrode 17 and the intermediate section 14. The connection tubing 24 has a single lumen which allows passage of the tip and ring electrodes lead wire, the sensor cable, thermocouple wires, the puller wires, and the irrigation tubing into the tip electrode 17. The single lumen of the connection tubing 24 allows these components to reorient themselves as needed from their respective lumens in the intermediate section 14 toward their location within the tip electrode 17. In the disclosed embodiment, the tubing 24 is a protective tubing, e.g., PEEK tubing, having a length ranging between 6 mm and 12 mm, more preferably about 1 lmm. It is noted that selected components, including the tip and ring electrode lead wires are not shown for better clarity of other components and structure of the tip electrode.

The shell 50 is constructed of a biocompatible metal, including a biocompatible metal alloy. A suitable biocompatible metal alloy includes an alloy selected from stainless steel alloys, noble metal alloys and/or combinations thereof. In one embodiment, the shell is constructed of an alloy comprising about 80% palladium and about 20% platinum by weight. In an alternate embodiment, the shell is constructed of an alloy comprising about 90% platinum and about 10% iridium by weight. The shell can formed by deep-drawing manufacturing process which produces a sufficiently thin but sturdy shell wall that is suitable for handling, transport through the patient's body, and tissue contact during mapping and ablation procedures. In a disclosed embodiment, the shell wall has a generally uniform thickness ranging between about 0.003 in and 0.010 in, preferably between about 0.003 in and 0.004 in, and more preferably about 0.0035 in. While the deep drawn method is well suited to manufacturing the shell with a sufficiently thin wall, it is understood that other methods, such as drilling and/or casting/molding, can also be used.

In the disclosed embodiment, there are 56 ports, arranged in six circumferential rows, where five rows R1-R5 have 10 ports each, and a distal row R6 has six ports. The ports of rows R1-R5 are generally equidistant from each other, although the ports of adjacent rows are offset from each other such that each port is equidistant to four or six adjacent ports. A most distal ten-port row R5 is located at the rounded distal portion of the shell. The row (or circle) R6 is on a flat or nearly flat distal end 53 of the shell. The six ports of the row R6 are equi-angular on the circle.

The ring electrodes 22 which are mounted on the connection tubing 24 can be made of any suitable solid conductive material, such as platinum or gold, preferably a combination of platinum and iridium. The ring electrodes can be mounted onto the connection tubing 24 with glue or the like. Alternatively, the ring electrodes can be formed by coating the tubing 24 with an electrically conducting material, like platinum, gold and/or iridium. The coating can be applied using sputtering, ion beam deposition or an equivalent technique. The number of the ring electrodes on the tubing 24 can vary as desired. The rings may be monopolar or bi-polar. In the illustrated embodiment, there is a distal monopolar ring electrode and a proximal pair of bi-polar ring electrodes. Each ring electrode is connected to a respective lead wire. The tip electrode 17 is electrically connected to a source of ablation energy by the lead wire. The ring electrodes 22 are electrically connected to an appropriate mapping or monitoring system by respective lead wires.

The tip electrode of the present invention can operate at about 8 ml/minute or lower for wattage below 30 and about 17 ml for wattage between 30 and 50. The reduction in fluid-loading on the patient in a five or six hour procedure can thus be very significant. Moreover, where the flow rate is regulated by a programmable pump, the flow rate can even be lower for lower wattage.

Figure 6:
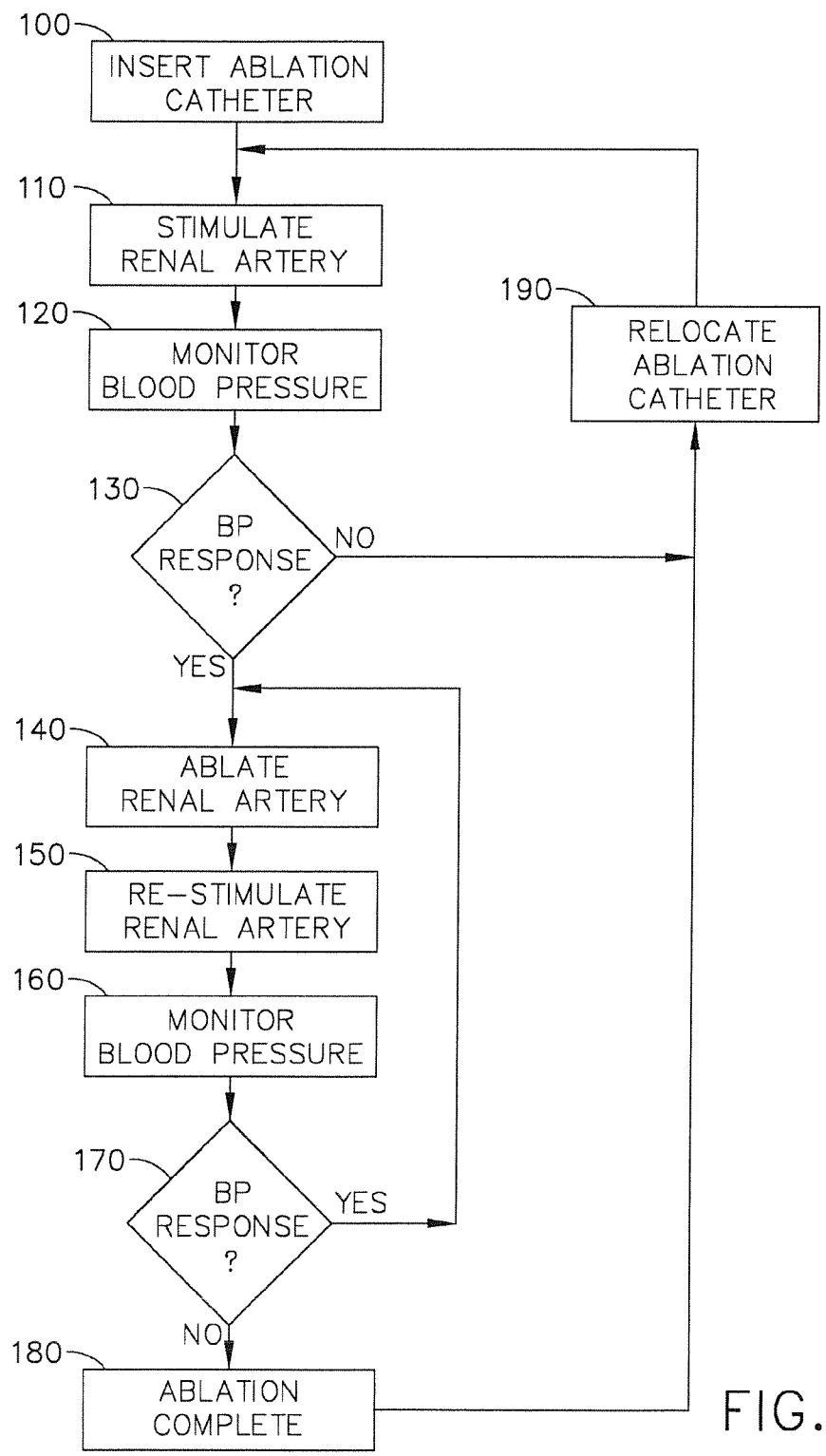
FIG. 6 is a flow diagram of the method of renal denervation in accordance with the present invention.

FIG. 6 is a flow diagram depicting the process for the dual ablation procedure in accordance with the present invention. At step 100, the physician inserts of the ablation catheter into the renal artery of the patient to be treated. This may be accomplished through an incision into the renal artery and navigation of the ablation catheter into the renal artery or through another known method. The location at which to apply the rf ablation energy is determined by using high-frequency stimulation, preferably at a frequency greater than 20 KHz at step 110. Using high-frequency stimulation it can be determined if a renal nerve is in the vicinity of the ablation catheter. High-frequency stimulation of a renal nerve will cause a drop in the blood pressure of the patient, thus, the blood pressure of the patient is monitored at step 120. At step 130 if a drop in blood pressure is seen in response to the high-frequency stimulation then at step 140 the tissue may be ablated. The ablation catheter is used to ablate the renal nerve. For example, using the irrigated rf ablation catheter described above rf energy can then be applied to this spot on the inside of the renal artery resulting in ablation of the renal nerve. Cooling fluid from the irrigated ablation catheter will protect the endothelial and smooth muscle cells from excessive damage so as to avoid the possibility of renal stenosis. The cooling fluid should be sufficiently cool to reduce damage to the endothelial layer, it should be preferably cooler than the body temperature of the patient and, more preferably, below approximately, 20 degrees Celsius. Rather than using rf energy, the ablation catheter may use ultrasound or microwave radiation or a cryogen as is known in the art.

Confirmation of a successful ablation is achieved by using the same high-frequency stimulation to re-stimulate the same tissue at step 150 to determine if there is a lack of a vagal response, i.e., a lack of a drop in blood pressure of the patient when the same area is stimulated in the same manner. By monitoring the blood pressure at step 160 and determining whether or not there is a response at step 170, the ablation of the renal nerve near that location can be confirmed at step 180 or, if there is still a response in the blood pressure due to stimulation, the ablation can be repeated at step 140. Once the ablation is confirmed through a lack of vagal response at either step 130 or step 170 the ablation catheter may be relocated at step 190 to determine if there are other areas of the renal artery that include a renal nerve that requires ablation to achieve the desired result.

High-frequency stimulation is accomplished through the use of a generator from Grass Technologies greater than or equal to 20 KHz.

For the specific treatment of a cardiac arrhythmia the next step in the process is to insert an ablation catheter into the femoral or brachial artery of the patient and to navigate the ablation catheter into a chamber of the heart to perform an ablation of cardiac tissue. In the case of atrial fibrillation, ablation is performed to achieve isolation of one or more pulmonary veins. The ablation catheter is introduced into an incision an introducer catheter in the femoral artery of the patient and is navigated into the atria of the heart, for example, in accordance with the teachings of United States Patent Publication No. 2007/0032826 by Y. Schwartz entitled "Standardization of Catheter Based Treatments for Atrial Fibrillation". The combination of renal nerve denervation and pulmonary vein isolation provides an improved reduction in the recurrence of atrial fibrillation in patients resulting in a reduction in repeat procedures.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A method for a treatment of a patient comprising:
    inserting an ablation catheter having an irrigated tip electrode mounted thereon into a renal artery of a patient wherein the renal artery has a wall defining a lumen, the irrigated tip electrode comprising a shell including a plurality of fluid ports and an internal member including a fluid inlet having an inlet aspect ratio greater than 1.0, wherein the irrigated tip electrode has a diffusion ratio of less than 2.0;
    heating a portion of the wall of the lumen of the renal artery with the irrigated tip electrode;
    irrigating at least the portion of the wall with a cooling fluid that exits the plurality of fluid ports; and
    ablating a renal nerve of the renal artery.

2. The method of claim 1, wherein the step of heating the portion of the wall of the lumen of the renal artery includes providing the irrigated tip electrode with a wattage that ranges from 30 watts to 50 watts and the step of irrigating at least the portion of the wall with the cooling fluid includes flowing the cooling fluid at a flow rate that equals 17 ml/min.

3. The method of claim 1, wherein a wattage is less than or equal to 30 watts and a flow rate is less than or equal to 8 ml/min.

4. The method of claim 1, wherein the plurality of fluid ports includes fifty fluid ports arranged in circumferential rows around the irrigated tip electrode and six fluid ports in a circle on a flat distal end of the irrigated tip electrode.

5. The method of claim 1, wherein a temperature of the cooling fluid is less than a body temperature of the patient.

6. The method of claim 1, wherein the cooling fluid comprises saline.

7. The method of claim 1, wherein heating a portion of the wall of the lumen of the renal artery comprises using radio frequency energy.

8. The method of claim 1, further comprising:
    stimulating a portion of the wall of the lumen of the renal artery at a frequency greater than 20 KHz;
    monitoring a blood pressure of the patient; and
    identifying a location of the wall of the lumen of the renal artery where the stimulation causes a decrease in the blood pressure of the patient, thereby indicating the presence of the renal nerve near the location.

9. The method of claim 8, wherein the ablating step comprises ablating tissue proximate to the location of the wall of the lumen.

10. The method of claim 9, wherein the ablation catheter is moved to a second location and the steps of stimulating, monitoring, identifying and ablating are repeated.

11. The method of claim 10, wherein the step of monitoring the blood pressure of the patient is performed before and during the step of stimulating the portion of the wall of the lumen.

12. The method of claim 10, wherein the step of monitoring the blood pressure of the patient is performed before and after the step of stimulating the portion of the wall of the lumen.

13. The method of claim 10, further comprising:
    re-stimulating the location to determine whether the stimulation decreases the blood pressure of the patient;
    re-monitoring the blood pressure of the patient due to the re-stimulation; and
    re-ablating the identified location.

14. The method of claim 13, further comprising repeating the steps of re-stimulating, remonitoring, and re-ablating, until the re-stimulating does not cause a decrease in the blood pressure.

15. The method of claim 1, in which the internal member comprises a plug member that includes the fluid inlet.

16. The method of claim 15, in which the inlet aspect ratio is defined as a ratio between a greater dimension of the fluid inlet and a lesser dimension of the fluid inlet, and in which the ablation catheter has an inner diameter of 0.061 inches to 0.065 inches such that the greater dimension is smaller than the inner diameter.

17. The method of claim 16, in which the internal member further comprises a baffle member.

* * * * *